United States Patent [19]
Abshire et al.

[11] Patent Number: 5,083,910
[45] Date of Patent: Jan. 28, 1992

[54] INSOLE ASSEMBLY BASE COMPONENT MOLDING PAD

[76] Inventors: Danny P. Abshire; Jennifer M. Abshire, both of 633D S. Broadway, Boulder, Colo. 80303

[21] Appl. No.: 527,660

[22] Filed: May 17, 1990

Related U.S. Application Data

[63] Continuation of Ser. No. 231,077, Aug. 11, 1988, abandoned.

[51] Int. Cl.⁵ .................. B29C 33/40; B29D 31/00
[52] U.S. Cl. .................. 425/2; 264/222; 264/DIG. 30; 249/55; 425/171; 425/173; 425/119
[58] Field of Search ............ 425/2, 119, 171, 173; 264/222, 223, DIG. 30; 249/54, 55, 217

[56] References Cited

U.S. PATENT DOCUMENTS

| | | | |
|---|---|---|---|
| 2,472,754 | 6/1949 | Mead | 264/223 |
| 2,547,419 | 4/1951 | Sugarman et al. | 264/223 |
| 3,309,447 | 3/1967 | Wegley | 264/223 |
| 3,458,898 | 8/1969 | Casparis | 425/2 |
| 4,139,337 | 2/1979 | David et al. | 425/2 |
| 4,522,777 | 6/1985 | Peterson | 425/2 |
| 4,548,563 | 10/1985 | Aigrefeuille | 425/2 |
| 4,747,989 | 5/1988 | Peterson | 425/2 |
| 4,927,584 | 5/1990 | Pfrimmer | 425/2 |

FOREIGN PATENT DOCUMENTS 943586 12/1963 United Kingdom .................. 425/2

OTHER PUBLICATIONS

"Orthotics", Foot Levelers, Inc., 2 pages.

*Primary Examiner*—Jay H. Woo
*Assistant Examiner*—Khanh Nguyen
*Attorney, Agent, or Firm*—John R. Flanagan

[57] ABSTRACT

A custom-fitted insole assembly for use in a shoe directly under a wearer's foot includes a heel-cupping and arch-supporting base component custom contoured to fit the heel and arch of the wearer's foot, a heel stabilizing component attached to an underside heel region of the base component, and a shock absorbing top sheet component sized to underlie the bottom of the wearer's foot and at its rear half to overlie and conform to the contour of the base component. Apparatus for custom fitting the base component of the insole assembly uses a support stand having a transparent window on which the wearer stands for examining the wearer's weighted feet to determine foot type, and a molding pad composed of at least one gel bag of flowable material disposable on the transparent window after the examination is completed for molding under the wearer's weighted foot a heated base component blank into the heel-cupping and arch-supporting base component of the insole assembly so as to custom contour the base component to fit the heel and arch of the wearer's foot.

3 Claims, 6 Drawing Sheets

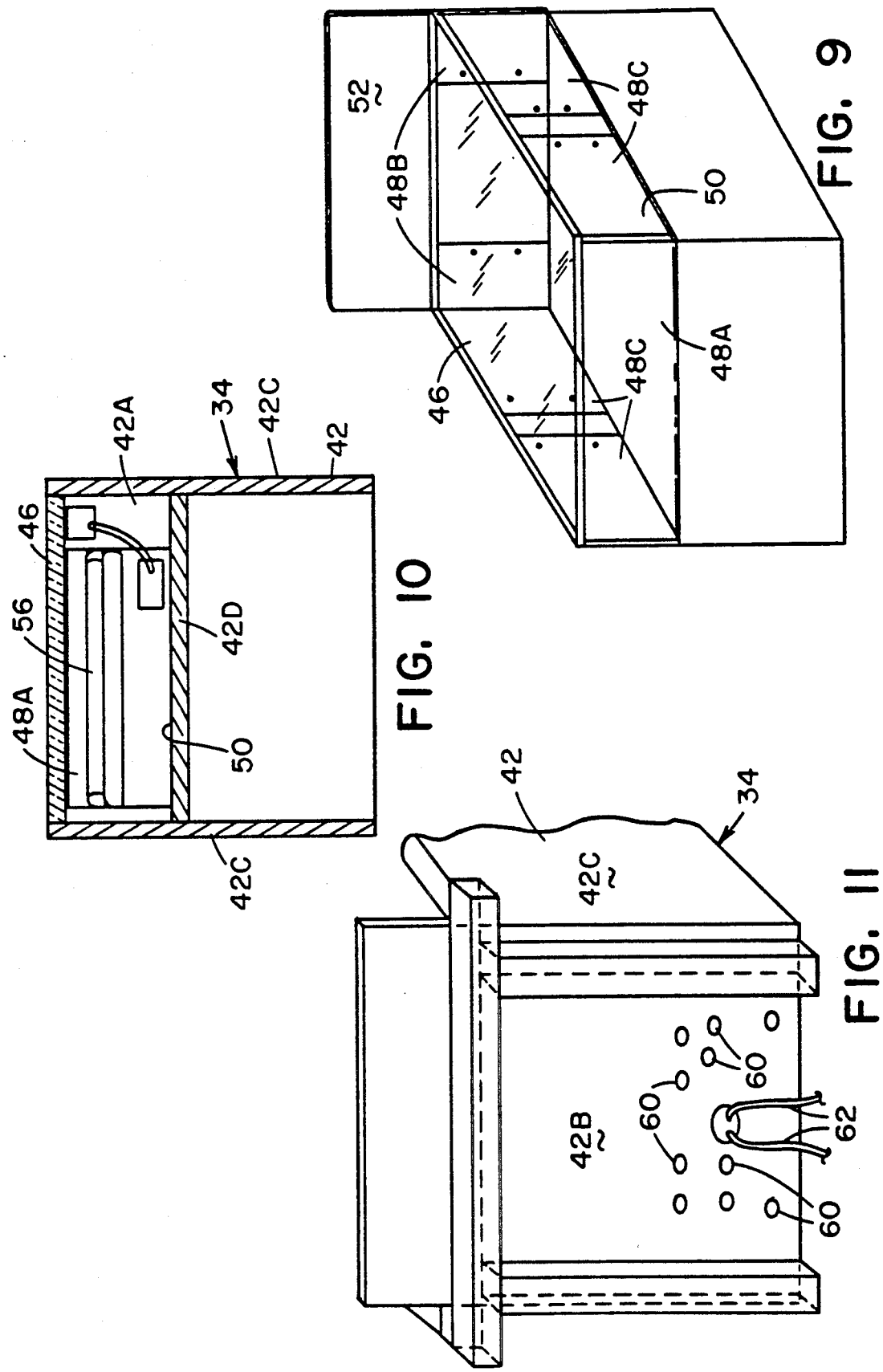

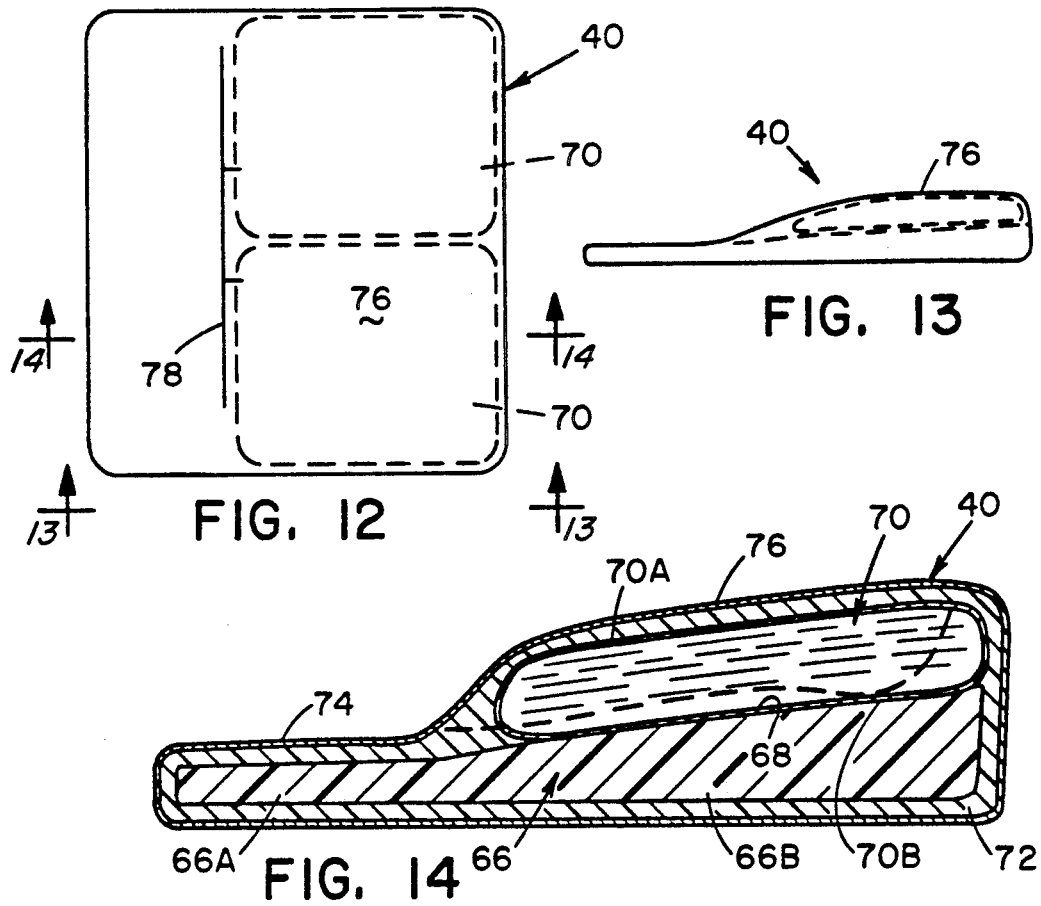
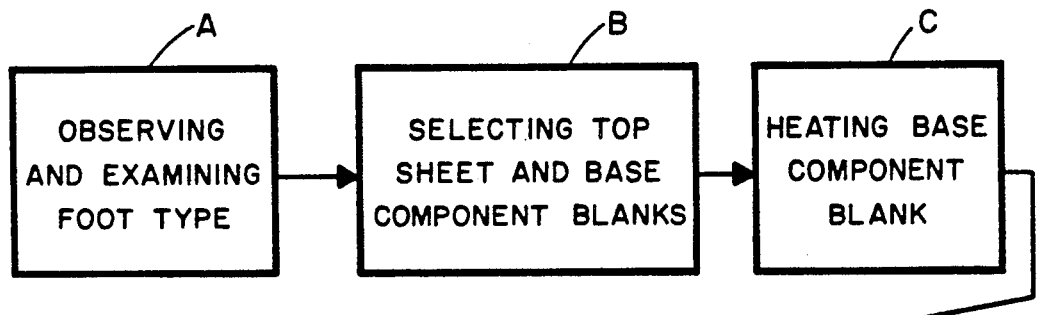
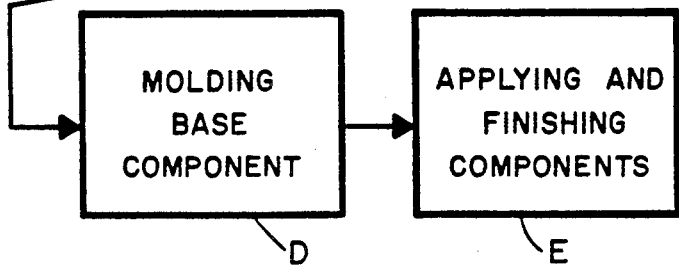
FIG. 15

INSOLE ASSEMBLY BASE COMPONENT MOLDING PAD

This application is a continuation of application Ser. No. 07/231,077, filed Aug. 11, 1988 now abandoned.

BACKGROUND OF THE INVENTION

1. Field of the Invention

The present invention generally relates to the art of enhancing shoe comfort and support and, more particularly, is concerned with a custom-fitted insole assembly and a method and apparatus for custom making the insole assembly.

2. Description of the Prior Art

An insole is a component of a shoe which overlies a bottom heel and sole of the shoe and on which the wearer's foot directly rests. Standard or generic insoles are produced at the shoe factory and thus are not formed specifically or customized to fit the feet of the ultimate wearer of the shoes. Most standard insoles are removable and replaceable. Although such insoles are intended to improve shoe comfort and support, they are probably as likely to lead to ill-fitted shoes which will tend to aggravate any problems already present such as due to certain destabilizing conditions exhibited by many wearers' feet.

Feet of many wearers typically are of one of two different unstable types or combinations of both. Over-pronated, floppy or flexible, foot is one unstable type. Pronation as applied to a human foot is a combination of movements of the bones and joints of the foot which results in lowering of its longitudinal arch in a way providing a normal shock absorbing mechanism. This action of the foot from a neutral position to about four degrees inwardly, helps absorb the impact of the step. Over-pronation refers to excessive inward rotation of the foot more than four degrees and particularly hinging of the foot from side to side thus the floppy appearance. The over-pronated foot appears to have a low or fallen arch, looking straight and flat on the medial side. This can lead to several problems including pressure on hips and lower back, interior or exterior knee pain, shin splints, achilles tendon problems, heel spurs and plantar faciitis, ankle pain, and bunions.

Supinated, rigid or under-pronated, foot is the other unstable type. In the supinated type, the foot predominately levers or moves back to front—heel to forefoot. Because of the lack of inward rotation, this foot-type is a poor shock absorber. Since a supinated foot is so rigid, the knees, lower back, and hips compensate to absorb the extra stress and shock the foot fails to do. The foot appears to have a high arch and a more curved appearance on the medial edge. The body's weight is placed on the forefoot and heel, more to the lateral edge of the foot than to the medial edge as in the pronated foot. When walking the foot seems to roll on the lateral edge of the foot. Because of this rigid movement, there is no weight distribution in the arch or midfoot area. Because of uneven weight distribution and lack of arch support, the supinated foot-type is prone to several injuries: meditarsal and heel problems, plantar fasciitis, heel spurs, shin splints, and knee pain on the lateral edge.

A third foot type is the desired one, commonly referred to as a stable or neutral foot. A neutral foot is one that is stable from side to side, does not tend to over rotate or excessively roll to the medial or lateral edge, and has a neutral line down the medial edge of the foot. Because the foot is naturally in a neutral position, this foot-type has the normal pronation at the end of the walking gait. The foot has an average arch height. This indicates that the foot does not have the low arch due to over-pronation, nor an extremely high arch like that of the rigid foot. The stable foot type also has a naturally even weight distribution throughout the base of the foot; equal weight on heel, lateral edge of midfoot, onto the forefoot and toes. This foot type is substantially free of apparent problems.

The objective of an insole should be to compensate for the different unstable foot types in a manner which provides a more neutral and stable base that better holds and supports the foot. Unfortunately, none of the standard or generic insoles come close to achieving this objective. The same is true of so-called "custom-fitted" insoles currently in use.

As a consequence, it is readily apparent that a need still exists for a stabilizing and neutralizing insole and a way in which to produce the same.

SUMMARY OF THE INVENTION

The present invention provides a custom insole system designed to satisfy the aforementioned needs. The custom insole system of the present invention relates to a custom-fitted insole assembly and a method and apparatus for custom making the same. The custom insole system of the present invention permits a wearer to have an insole assembly tailored specifically to help with added stability in all foot types and enhance comfort and support for those foot types in their specific shoes. The custom insole system benefits the over-pronated foot type by providing more lateral stabilizing support in the heel and ankle area. The custom insole system benefits the supinated foot type by being contoured to the individual arch helping to distribute body weight more evenly. A cushioned heel component is applied to absorb shock and a top sheet component is used to protect the forefoot and meditarsals from impact. The stable foot-type is also benefited by the custom insole system of the present invention by giving the wearer a custom feel in all his or her shoes and by adding more comfort and support. The personalized fit aids in increased athletic performance and adds protection to the whole foot. The stable foot's natural comfort and support is now enhanced by personalizing shoes which were originally made to fit millions of different feet.

The custom insole assembly basically includes a heel-cupping and arch-supporting base component, a heel stabilizing component and a shock absorbing top sheet-like component. The base component is molded under the wearer's foot while weighted by the wearer poised in a standing position in contrast to a method which takes an impression of a wearer's foot while unweighted by the wearer in a sitting position and then makes an insole from a mold made from the impression. The stablized heel component adds extra shock absorption; the base component provides a personalized arch adding superior support and comfort; and the top sheet provides extra shock absorption and protection of the forefoot.

Uniquely, the method and apparatus for custom making the base component of the insole assembly employs a gel-molding pad for supporting the weighted foot that readily conforms to the configuration of the bottom of the foot. With the wearer actually standing, the gel-molding pad permits the taking of a relatively neutral impression of the foot and thereby allows the molding of a neutral imprint of the foot in the base component of the insole assembly.

The method and apparatus of the insole system also uses a stand having a window and mirror arrangement for facilitating examination and analysis of the wearer's foot prior to molding of the base component to identify the foot type and any possible unstable characteristics of the foot. After molding of the base component is completed, certain other steps such as grinding and trimming are carried out in finishing the base component and combining it with a heel stablizing component and a top sheet component to complete the insole assembly.

Accordingly, the present invention is directed to a custom-fitted insole assembly for use in a shoe directly under a wearer's foot. The insole assembly comprises: (a) a heel-cupping and arch-supporting base component custom contoured to fit the heel and arch of a wearer's foot; (b) a heel-stabilizing component attached to an underside rear region of the base component; and (c) a shock absorbing top sheet component sized to underlie the bottom of a wearer's foot and at its rear portion to overlie and conform to the contour of the base component.

Also, the present invention is directed to a method of custom fitting a base component of an insole assembly for use in a shoe directly under a wearer's foot. The custom-fitting method comprises the steps of: (a) heating a blank of the base component material of the insole assembly material to a temperature above its setting point; and (b) molding the heated blank of base component material under a foot of the wearer while weighted by the wearer poised in the standing postion into a heel-cupping and arch-supporting base component of the insole assembly so as to custom contour the base component to fit the heel and arch of the wearer's foot. Further, the method comprises the step of examining the wearer's weighted foot to determine foot type while the wearer is poised in the standing position on a transparent window of a support stand. Also, the method comprises the step of making the remaining components of the insole assembly by finishing and attaching a heel stabilizing component of the insole assembly to an underside heel region of the base component, and finishing a separate shock absorbing top sheet component of the insole assembly sized to underlie the bottom of the wearer's foot and at its rear portion to overlie and conform to the contour of the base component.

Further, the present invention is directed to apparatus for custom fitting a base component of an insole assembly for use in a shoe directly under a wearer's foot. The custom-fitting apparatus comprises: (a) means for heating a blank of the base component material of the insole assembly material to a temperature above its setting point; and (b) means for molding the heated base component blank under a foot of the wearer while weighted by the wearer poised in the standing position into a heel-cupping and arch-supporting base component of the insole assembly so as to custom contour the base component to fit the heel and arch of the wearer's weighted foot. The apparatus also comprises means for supporting the wearer in the standing position to impose weight on the foot of the wearer and permitting examining of the wearer's weighted foot for determining the wearer's foot type.

More particularly, the supporting means includes a support stand having a transparent window adapted to support the wearer standing thereon and a chamber disposed below the window. A mirror is located in the chamber below the window for permitting observation and examination of the bottom of the wearer's feet while standing on the window.

Further, the molding means includes a molding pad of flowable material for supporting the wearer's weighted foot in a neutral position and being capable of taking on a relatively neutral impression of the configuration of the bottom of the wearer's weighted foot, thereby allowing forming of the heated blank of base component material into a relatively neutral imprint of the wearer's weighted foot in the base component. Still further, the molding pad includes a semi-rigid foam base having a generally inclined upper surface being at a greater height at a rearward portion than a forward portion thereof, and at least one gel bag disposed on the upper surface of the foam base along the rearward portion thereof. A flexible plastic material encases the base and gel bag.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the course of the following detailed description, reference will be made to the attached drawings in which:

FIG. 9 is an perspective view of the stand similar to FIG. 8 but only of the construction of the components forming the inside of the stand.

FIG. 10 is a rear view of a front portion of the stand taken along line 10—10 of FIG. 8.

FIG. 11 is a fragmentary rear perspective view of the stand of FIG. 8.

FIG. 12 is an enlarged top plan view of the gel-molding pad of FIG. 7.

FIG. 13 is a side elevational view of the gel-molding pad as seen along line 13—13 of FIG. 12.

FIG. 14 is a longitudinal sectional view of the gel-molding pad taken along line 14—14 of FIG. 12, showing in solid line the pad before a weighted foot is standing thereon and in dashed line the pad after a weighted foot is standing thereon.

FIG. 15 is a flow diagram depicting the overall sequence of steps employed by a method of custom fitting the insole assembly in accordance with the principles of the present invention.

DETAILED DESCRIPTION OF THE INVENTION

Figure 1:
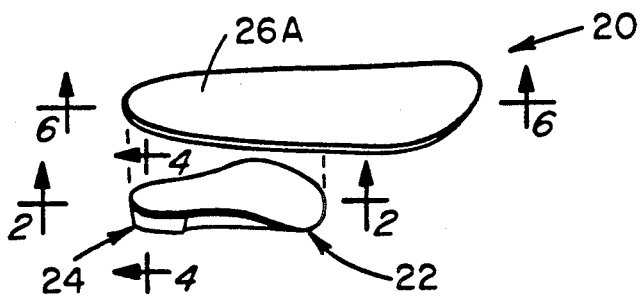
FIG. 1 is a perspective view of a custom-fitted insole assembly of the present invention.
Figure 2:
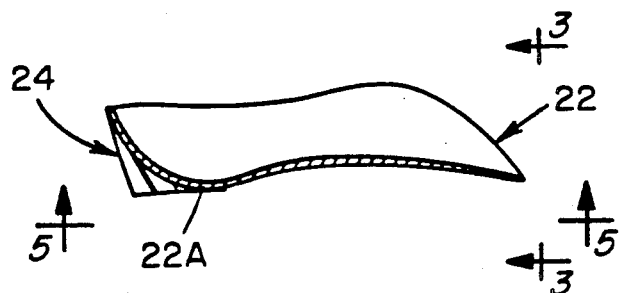
FIG. 2 is an enlarged longitudinal sectional view of base and heel components of the insole assembly taken along line 2—2 of FIG. 1.
Figure 3:
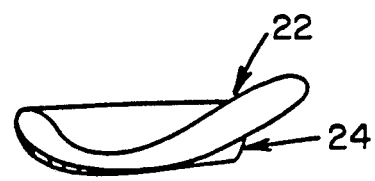
FIG. 3 is a front elevational view of the base and heel components of the insole assembly as seen along line 3—3 of FIG. 2.
Figure 5:
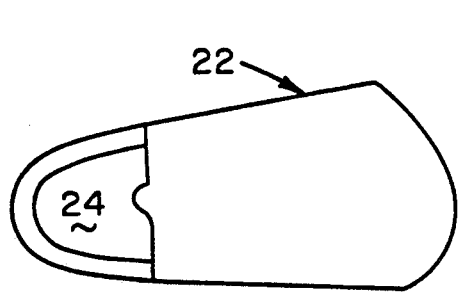
FIG. 5 is an enlarged bottom plan view of the base and heel components of the insole assembly as seen along line 5—5 of FIG. 2.
Figure 4:
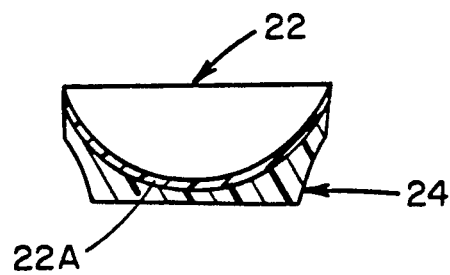
FIG. 4 is an enlarged cross-sectional view of the base and heel components of the insole assembly taken along line 4—4 of FIG. 1.
Figure 6:
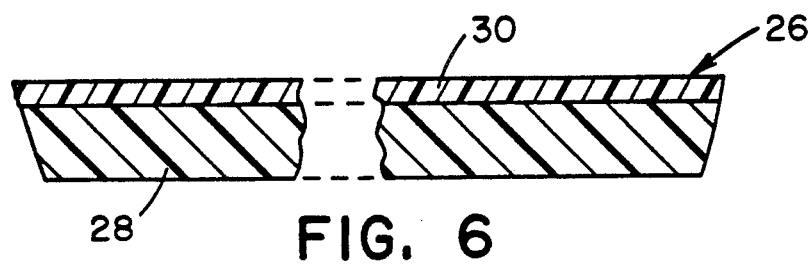
FIG. 6 is an enlarged foreshortened longitudinal sectional view of a top sheet component of the insole assembly taken along line 6—6 of FIG. 1.
Figure 8:
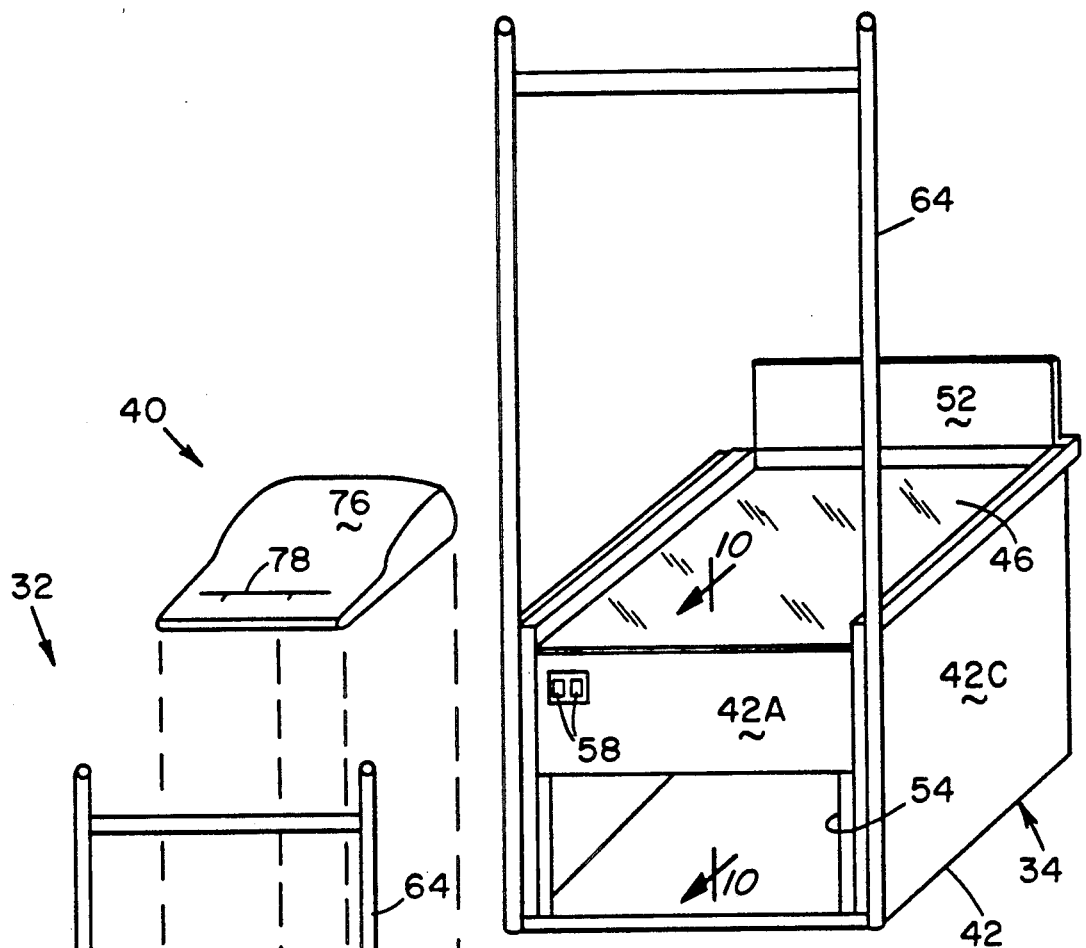
FIG. 8 is an enlarged front perspective view of a stand of the custom insole assembly fitting apparatus of FIG. 7.

Referring now to the drawings, and particularly to FIGS. 1-6, there is shown a custom-fitted insole assembly, being generally designated by the numeral 20 and constructed in accordance with the principles of the present invention. The insole assembly 20 being custom-fitted to a wearer's weighted foot is intended for use in any type of shoe (i.e., running, hiking, walking, etc.) of the wearer directly under the wearer's foot in place of a standard or generic removable insole made in the factory with the shoe.

In its basic components, the custom insole assembly 20 includes a heel-cupping and arch-supporting base component 22 custom contoured to fit the heel and arch of the wearer's foot, a heel stabilizing component 24 attached to an underside heel region 22A of the base component 22, and a shock absorbing top sheet component 26 sized to underlie the bottom of the wearer's foot and at a rear portion 26A of the top sheet 26 to overlie and conform to the contour of the base component 22.

More particularly, the base component 22 of the insole assembly 20 is preferably composed of a lightweight thermal moldable plastic material having a low molding temperature and capable of retaining its molded shape so that it is supportive but flexible. The setting temperature of a suitable moldable plastic material is, for example, in a range where the material can be handled by the person doing the custom molding. One example of a suitable material is Polysar X414 having a setting point of around 90 degrees F. Use of other materials is possible.

The heel stabilizing component 24 of the insole assembly is preferably a dense, resilient and shock absorbent material. One example of a suitable material is ¼" Poron identified by the generic name "blue bully". In addition to being dense, resilient and shock absorbent, other characteristics of this material are: easy fabrication, low compression set, internal strength and dimensional stability, long lasting and hygenic. Another example of a suitable material is ¼" 12 Iron Trendair Crepe identified by the generic name "crepe". In addition to being resilient and shock absorbent, other characteristics of this material are: oil resistant, low compression set, internal strength and dimensional stability and long lasting.

The top sheet component 26 of the insole assembly is preferably composed of a lower layer 28 of a shock absorbent resilient foam material and an upper layer 30 of a water proof virgin vinyl material bonded to the lower layer 28. One example of a suitable shock absorbent foam for the lower layer 28 is Poron cellular urethane. In addition to being shock absorbent and resilient, other characteristics of this material are: easy fabrication and aesthetics, long lasting, hygenic, low compression set and internal strength and dimensional stability. One example of a suitable virgin vinyl for the upper layer 30 is Marine Naugahyde. In addition to being water proof, other characteristics of this material are: mildew treated, odor resistant, non-absorbent of perspiration and washable.

The overall features of the insole assembly 20, relative to the particular foot it is specifically custom fitted for, are multi-density, versatility and convertibility. With respect to the multi-density feature, the insole assembly is shock absorbent and flexible in the forefoot area, shock absorbent and firm yet flexible in the midsole or arch area, and shock absorbent and counter and anti-rotation supportive in the heel area.

With respect to the versatility feature, the custom-fitted right and left insole assemblies are made to fit into all of the wearer's shoes, whether they are for cycling, running, walking, working, hiking, etc. With respect to the feature of convertibility, different top sheet components 26 of varying thicknesses can be used with the same combined base and heel components 22, 24. For instance, a thinner top sheet component, such as 1/16 inch, can be used for tighter fitting shoes, whereas a thick top sheet component, such as ⅛ inch, can be used with most sport shoes replacing the generic insole insert which came with the shoes. In some instances, the base component 22 can be worn along without any top sheet component 24, such as in a very tight shoe. This will provide arch support and a heel craddle, but without the shock absorbent characteristic of the top sheet component 26.

In summary, the insole assembly 20 helps each wearer by supporting his or her feet in a neutral and stable position, flexing under pressure, and adding extra absorption and cushioning with each step. However, since the components do not absorb perspiration, the use of socks on the wearer's feet is recommended. The components can be cleaned easily with a damp cloth and soapy water.

Turning now to FIGS. 7-14, there is illustrated an apparatus, generally identified by the numeral 32, for custom fitting the insole assembly 20 to the wearer's foot for use in a shoe directly under the wearer's foot. In its basic components, the apparatus 32 includes means in the form of a support stand 34 for supporting the wearer in the standing position, means in the form of a heater 36 for heating a blank 38 (see FIG. 16) of the base component material to a temperature (for example, in the range of 200 to 250 degrees F), above its setting point (for, example 90 degrees F), and means in the form of a molding pad 40 for molding the heated base component blank 38 under a foot of the wearer (see FIG. 16) while weighted by the wearer poised in the standing position on the stand 34.

More particularly, as seen in FIGS. 7-11, the support stand of the apparatus 32, in addition to being used in the molding of the base component 22, has features which permit observation and examination of the wearer's weighted foot for determining the wearer's foot type prior to molding the base component 22. The support stand 34 includes a box-like base housing 42 composed of interconnected front, rear, side and bottom walls 42A-42D which define a chamber 44. A transparent window 46 closes the chamber 44 at the top of the housing 42 by being mounted on the top edges of a plurality of support blocks 48A-48C attached on the front, rear and side walls 42A-42C. The transparent window 46 is strong enough to support a wearer standing thereon with the wearer's weight imposed on his or her feet. A bottom mirror 50 is located in the chamber 44 spaced below and facing toward the window 46 for permitting observation and examination of the bottom of the wearer's feet while standing on the window 46 for determining the wearer's foot type. Thus, the support stand 34 is designed with a pediscope-type of an arrangement for examining the base of the foot. To actually see where the body weight is being placed on the feet helps to determine the foot type.

Another mirror 52 is positioned on the housing 42 at the rear of the window 46. The mirror 52 is mounted to and extends upright from the rear of the housing 42. The rear upright mirror 52 is used for observing the Achilles tendon of the wearer's foot as the base component 22 is being formed and imprinted by the wearer's weighted foot so as to ensure a neutral position of the foot during the molding of the base component 22.

The heater 36 of the apparatus 32 can be a conventional small oven, such as a toaster oven, or any other suitable heating mechanism. The heater 36 is disposed in the bottom of the housing 42 below the bottom wall 42D of the chamber 44 thereof. The heater 36, which is used to heat up the blank of base component material 38, is readily accessible through an opening 54 in the front of the housing 42 below the front wall 42A. Lights 56 are provided in the chamber 44, being mounted on the interior rear side of the front wall 42A. A switch 58 for operating the lights 56 is mounted on the exterior front side of the front wall 42A. Vent holes 60 and cords 62 for the heater 36 are provided through the rear wall 42B of the housing 42. Finally, a generally inverted U-shaped hand rail 64 is attached to, and extends in upstanding fashion from, the front corners of the housing 42.

As seen in FIGS. 7 and 12-14, the molding pad 40 of the apparatus 32 is adapted to be supported on the transparent window 46 of the support stand housing 42 for facilitating the molding of the base component 22 under the foot of the wearer while weighted by the wearer poised in the standing position on the window 46. The molding pad 40 is placed on the window 46 after observation and examination of the bottom of the wearer's foot has been completed and molding of the heel-cupping and arch-supporting base component 22 of the insole assembly 20 is ready to begin. The pad 40 is specifically adapted for supporting the wearer's weighted foot in a neutral position and for taking on a relatively neutral impression of the configuration of the bottom of the wearer's weighted foot for molding the heated base component blank 38 when placed under the wearer's foot into a relatively neutral imprint of the wearer's weighted foot to form the heel-cupping and arch-supporting base component 22 of the insole assembly 20 custom contoured to fit the heel and arch of the wearer's weighted foot.

More particularly, the molding pad 40 of the apparatus 32 includes a semi-rigid, preferably double layer, foam base 66 having an upper surface 68 and generally forward and rearward portions 66A, 66B, and at least one and preferably a pair of nontoxic flowable gel bags 70. The gel bags 70 have lower and upper surfaces 70A and 70B. At their lower surfaces 70A, the gel bags 70 rest on the upper surface 68 of the foam base 66 along the rearward portion 66B thereof. The upper surface 68 of the foam base 66 is generally inclined being at a greater height at the rearward portion 66B than the forward portion 66A thereof. The molding pad 40 further is composed a layer 72 of flexible plastic material, such as neoprene, encasing the foam base 66 and gel bags 70. The pad 40 has a cover 74, such as of cloth, which fits over the outer layer 72 of encasing material. The top surface 76 of the cover 74 is provided with reference markings 78 thereon to indicate placement of the wearer's foot for molding the heated base component blank 38 under the wearer's foot.

The flowable material in the gel bags 70 of the gel-molding pad 40 helps to take a more neutral impression of the wearer,s weighted foot. From their upper surfaces 70B, each of the gel bags 70 will take an impression of an arch and heel of a respective weighted foot of the wearer when the arch and heel of the foot is placed thereon. FIG. 14 shows in solid line the profile of the gel bags 70 and flexible layer 72 of the pad 40 before the weighted foot is standing thereon and in dashed line the profile of the gel bags 70 and flexible layer 72 of the pad after the weighted foot is standing thereon. It can be readily observed in FIG. 14 that the semi-rigid foam base 66 is not deformed by the weighted foot of the wearer and thus does not take any portion of the impression formed in the gel bags 70. A more neutral impression means that the neutral molded base component 22 helps to hold and support the foot better.

In an exemplary form, the molding pad is seventeen inches long by sixteen inches wide. The height is 2½ inches in the rear decreasing to 1½ inches for the last five inches toward the front. The 5-inch section is for the forefoot of the wearer to be placed on while molding is taking place. The two plastic covered non-toxic gel bags 70 on the rearward portion 66B of the foam base 66 are each 1½ inches high, 8½ inches wide and twelve inches long. This puts the gel bags 70 at approximately a twenty-five degree angle of incline from front to back. The reason for ramping the gel bags 70 is to take some of the body weight off of the rear of the foot to give an acceptable heel cup and arch impression in the heated blank 38 which will form the base component 22. The rear mirror 52 mounted at the rear of the stand housing 42 rises above the gel-molding pad 40 so that the Achilles tendon can be observed to make sure it looks straight as molding of the base component 22 occurs. This helps to ensure a more neutral position.

Figure 7:
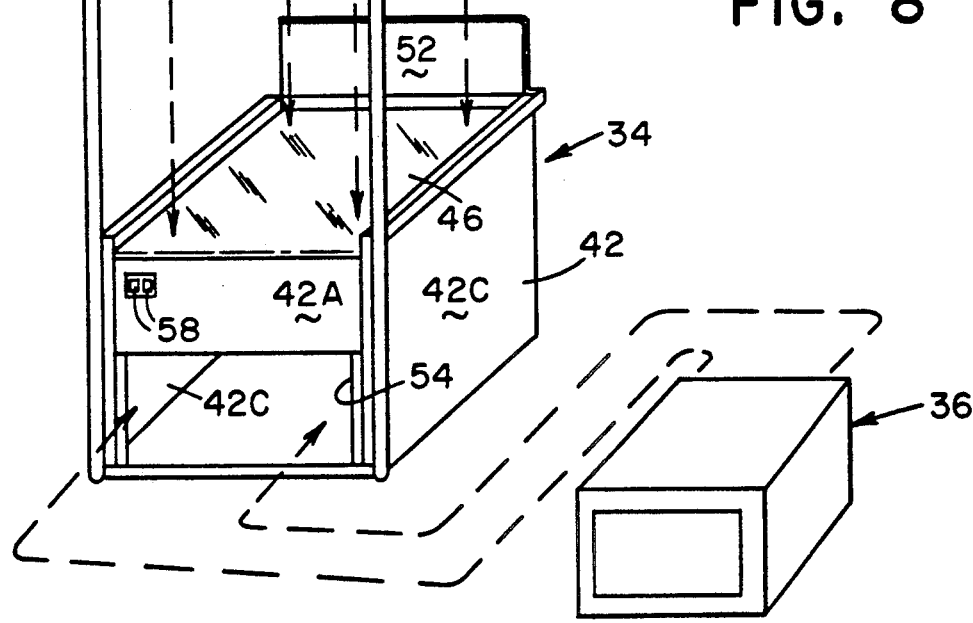
FIG. 7 is an exploded view of an apparatus for custom fitting the base component of the insole assembly in accordance with the principles of the present invention.
Figure 16:
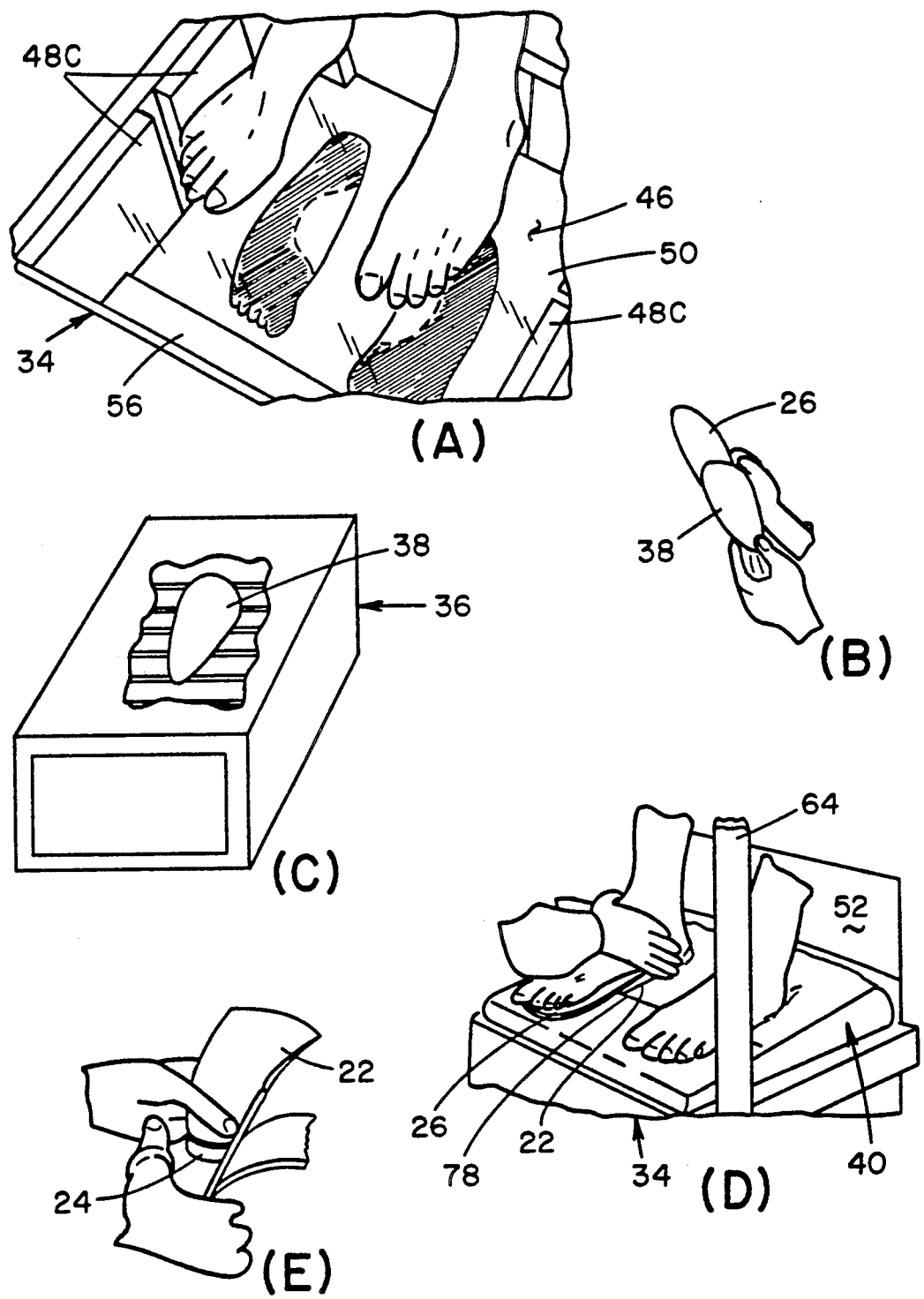
FIG. 16A, 16B, 16C, 16D and 16E are schematic representations of the method steps of FIG. 15.
Figure 16A:
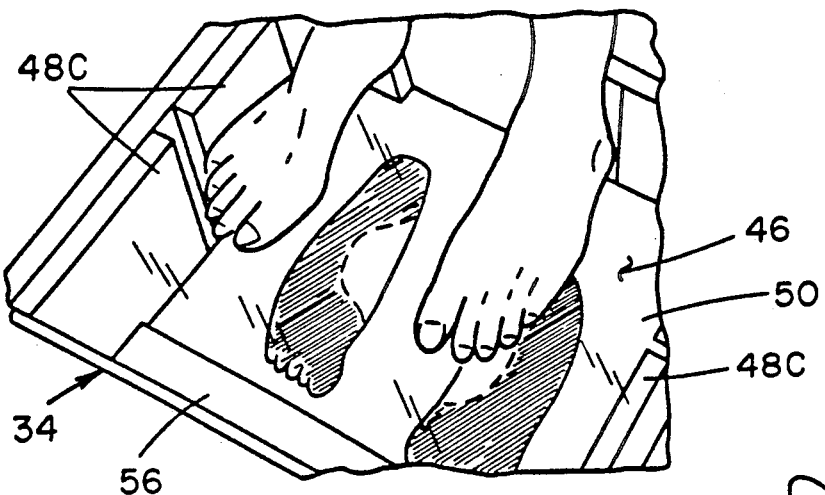
Figure 16B:
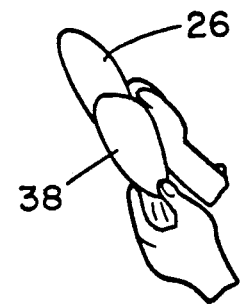
Figure 16C:
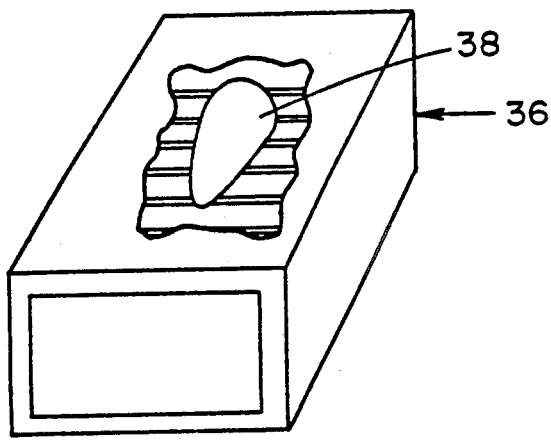
Figure 16D:
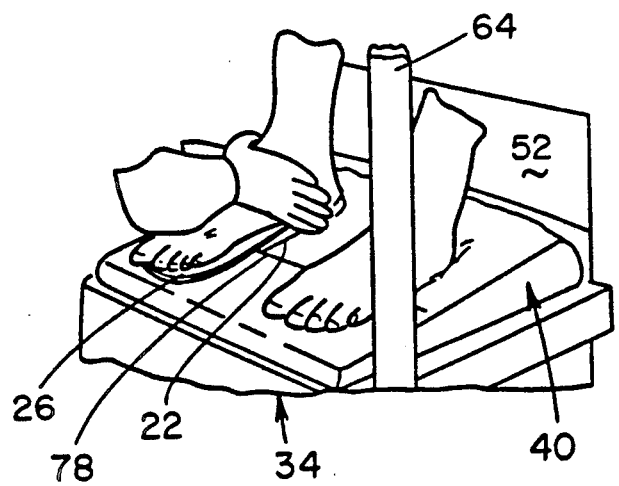
Figure 16E:
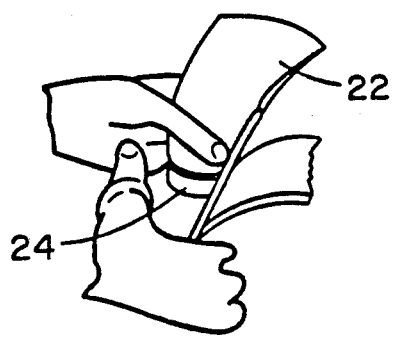

Referring now to FIGS. 15 and 16, there is depicted in flow chart and schematic forms the overall sequence of operative steps in the method which in accordance with the present invention employs the apparatus 32 of FIG. 7 for custom fitting the insole assembly 20 of FIG. 1 to a wearer's foot for use in a shoe directly under a wearer's foot. As denoted by block A of the flow diagram of FIG. 15 and depicted in (A) of FIG. 16, the first task is to determine the wearer's foot type by observing and examining the wearer's weighted foot while the wearer is poised in a standing position. The support stand 34 is employed for this purpose with the gel-molding pad 40 removed from the window 46. The wearer stands bare-footed on the transparent window 46 and the lights 56 are turned on, illuminating the bottom of his or her feet. The pressure of the foot bottom against the window 46 will be seen in the bottom mirror 50 below the window. Thus, prior to molding of the base component 22, the foot type and any possible unstable characteristics of the foot are identified.

Next, as denoted by block B of the flow diagram of FIG. 15 and depicted in (B) of FIG. 16, the second task is to select a top sheet component 26 and base component blank 38 for the particular wearer being served. Choose between small, medium and large sizes. The innersole can be taken form the wearer's shoes and the rough sizes of the components matched with portions of it. The base component must not restrict movement of the metatarsal (midfoot) area of the foot. If the small blank 38 is too small, the next size up can be used and cut back to about ½ inch behind the first metatarsal head. The blank 38 must fill three-fourths of the arch area. The top sheet component 26 should be the same length as the one removed from the wearer's shoes. It can always be trimmed.

The third task, as denoted by block C of the flow diagram of FIG. 15 and depicted in (C) of FIG. 16, is to heat base component blank 38 to a temperature above it setting point. The heater 36 is turned on to about 200 degrees F. and the blank 38 is placed in it. Then, according to block D in FIG. 15 and (D) in FIG. 16, the fourth task is to mold the heated base component blank 38 under the bare weighted foot of the wearer while the wearer is poised in the standing postion into a heel-cupping and arch-supporting base component 22 custom contoured to fit the heel and arch of the wearer's foot.

For this purpose, the gel-molding pad 40 is replaced under the wearer's foot back on the window 46. A base component 22 is first molded for one foot, and then for the other. The heated base component blank 38 should be flimsy and warm to its touch. The wearer lifts his or her foot up and to one side for allowing room for placing the heated blank 38 covered with a separate top sheet component 26 on the reference markings 78 on the molding pad 40. The wearer's bare weighted foot is then placed back on the top sheet component 26 overlying the base component. Weight is applied gradually and the foot is rolled to the outside and to the inside and returned to a neutral position so as to contour the molding pad 40 about the foot and achieve forming of a relatively neutral imprint of the wearer's weighted foot in the base component. The Achilles tendon of the wearer's foot is observed in the rear mirror 52 as the base component is being formed and imprinted by the wearer's weighted foot so as to ensure a neutral position of the foot during the molding of the base component 22. The wearer then stands with equal pressure on both feet, knees flexed slightly, until the temperature of the base component cools below its set-point. The procedure is repeated for the other foot.

The final tasks are denoted by block E of FIG. 15 and depicted in (E) of FIG. 16. They includes grinding and trimming the molded base component 22 to finish the same, and attaching the heel stabilizing component 24 to the underside heel regions of the base component 22 and finishing it by grinding it to the desired shape. Also, the tasks include finishing the separate shock absorbing top sheet component 26 by trimming it to underlie the bottom of the wearer's foot and at its rear portion 26A to overlie and conform to the contour of the base component 22. It is also desirable to bevel the peripheral edges of the components so that they make smooth transitions with adjacent portions of the wearer's shoe.

It is thought that the custom insole system of the present invention and many of its attendant advantages will be understood from the foregoing description and it will be apparent that various changes may be made in the form, construction and arrangement of the parts thereof without departing from the spirit and scope of the invention or sacrificing all of its material advantages, the form hereinbefore described being merely a preferred or exemplary embodiment thereof.

Having thus described the invention, what is claimed is:

1. An insole base component molding pad, comprising:
   (a) a semi-rigid base having an upper surface and generally forward and rearward portions, said rearward portion of said base being greater in height than said forward portion thereof and decreasing in height from rear to front of said rearward portion such that said upper surface of said rearward portion of said base is generally inclined downwardly and forwardly from said rear to front thereof, said forward portion of said base being generally constant in height such that said upper surface of said forward portion of said base is generally level from rear to front of said forward portion; and
   (b) at least one gel bag having an upper surface and an opposite lower surface, said gel bag at its lower surface resting solely upon said downwardly and forwardly inclined upper surface of said rearward portion of said base, said gel bag containing a flowable material being capable of taking on an impression of an arch and heel of a standing wearer's weighted foot when the arch and heel of the weighted foot is placed on said upper side of said gel bag resting upon said inclined upper surface of said rearward portion of said base and the forefoot of the wearer's weighted foot is placed on said upper surface of said forward portion of said base forwardly of said gel bag;
   (c) said semi-rigid base being composed of a material not deformable by the arch and heel of the wearer's weighted foot when supported on said gel bag such that said base is incapable of taking on any portion of the impression of the arch and heel of the weighted foot, said inclined upper surface of said rearward portion of said base upon which said gel bag solely rests correspondingly inclines said gel bag and said upper surface thereof downwardly and forwardly so as to cause transfer of the weight of the wearer from the arch and heel supported on said inclined upper surface of said gel bag to the forefoot of the foot supported on said upper surface of said forward portion of said base.

2. The molding pad as recited in claim 1, further comprising:
a flexible plastic material encasing said base and gel bag.

3. The molding pad as recited in claim 1, further comprising:
a cover having a top surface with reference markings thereon to indicate placement of a wearer's weighted foot for molding a base component under the wearer's foot.

* * * * *